United States Patent [19]

Hogan

[11] Patent Number: 4,842,586
[45] Date of Patent: Jun. 27, 1989

[54] SAFETY DEVICE AND METHOD FOR REMOVAL AND DISPOSAL OF MEDICAL NEEDLES

[75] Inventor: John M. Hogan, Long Beach, Calif.

[73] Assignee: City of Hope National Medical Center, Duarte, Calif.

[21] Appl. No.: 27,251

[22] Filed: Mar. 18, 1987

[51] Int. Cl.⁴ .............................................. A61M 5/32
[52] U.S. Cl. ...................................... 604/192; 604/198
[58] Field of Search ................................ 604/192–198, 604/263

[56] References Cited

U.S. PATENT DOCUMENTS

| | | | |
|---|---|---|---|
| 3,134,380 | 5/1964 | Armao | 604/198 |
| 4,373,526 | 2/1983 | Kling | 604/198 |
| 4,675,005 | 6/1987 | DeLuccia | 604/198 |
| 4,695,274 | 9/1987 | Fox | 604/198 |
| 4,702,738 | 10/1987 | Spencer | 604/263 |
| 4,723,943 | 2/1988 | Spencer | 604/263 |
| 4,725,267 | 2/1988 | Vaillancourt | 604/198 |
| 4,735,618 | 4/1988 | Hogen | 604/198 |
| 4,738,663 | 4/1988 | Bogan | 604/198 |

Primary Examiner—C. Fred Rosenbaum
Assistant Examiner—Mark F. Colosimo
Attorney, Agent, or Firm—Edward S. Irons

[57] ABSTRACT

A protective device and method for the removal and disposal of spinal needles. The protective device is comprised of a needle pulling assembly upon which is slidably mounted an external housing. In operation, a needle to be removed from a patient is engaged in the needle cradle portion of the needle pulling assembly. The external housing is moved into contact with the patient's skin and the needle is withdrawn by pulling on the pulling rod portion of the needle pulling assembly in a direction away from the patient. The needle is withdrawn into the interior of the external housing, thereby covering the entire length of the needle. The pulling assembly is then locked into place and the entire assembly including the withdrawn needle can be disposed of, thereby avoiding the possibility of needle pricks by contaminated spinal needles.

9 Claims, 3 Drawing Sheets

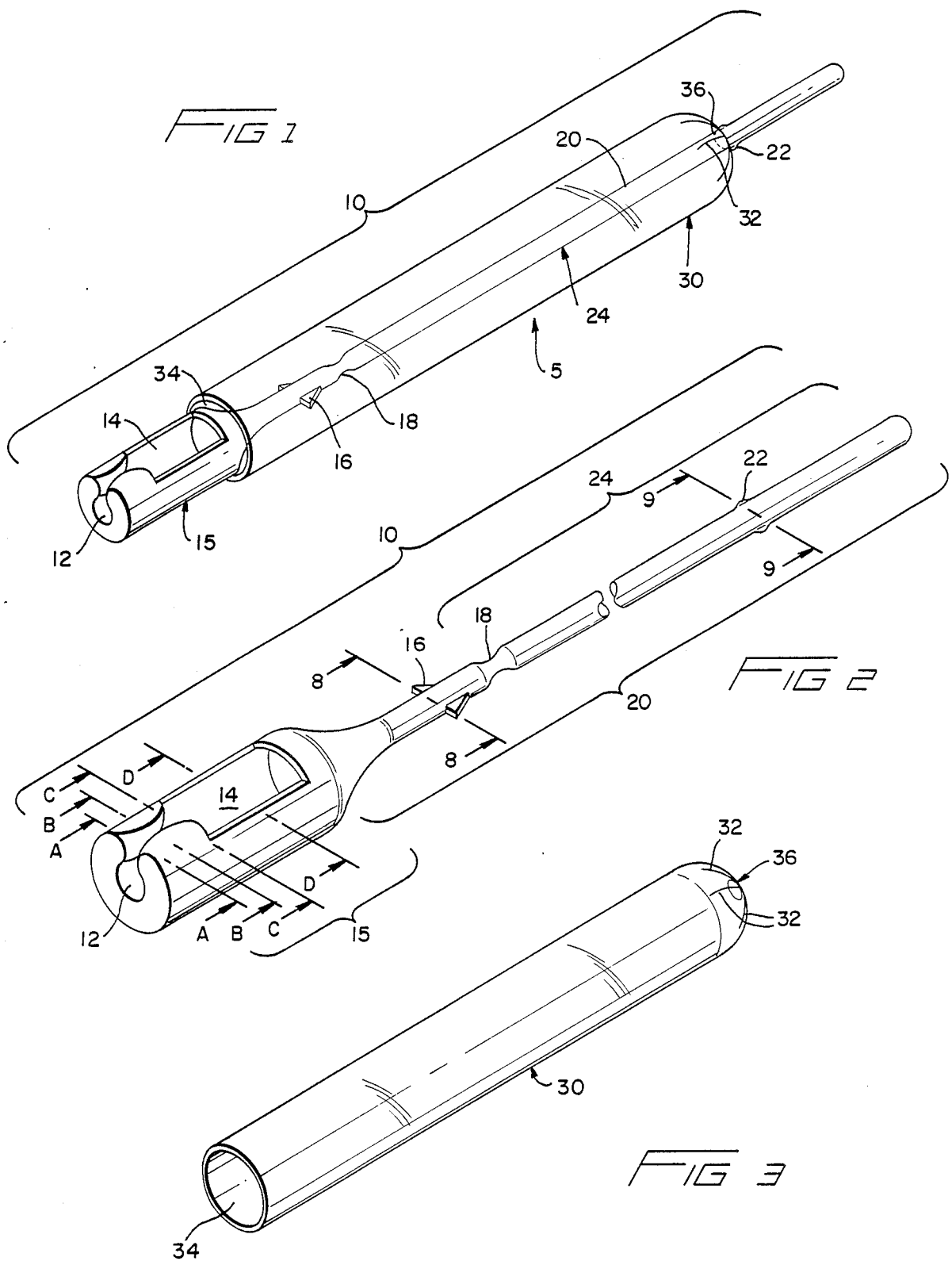

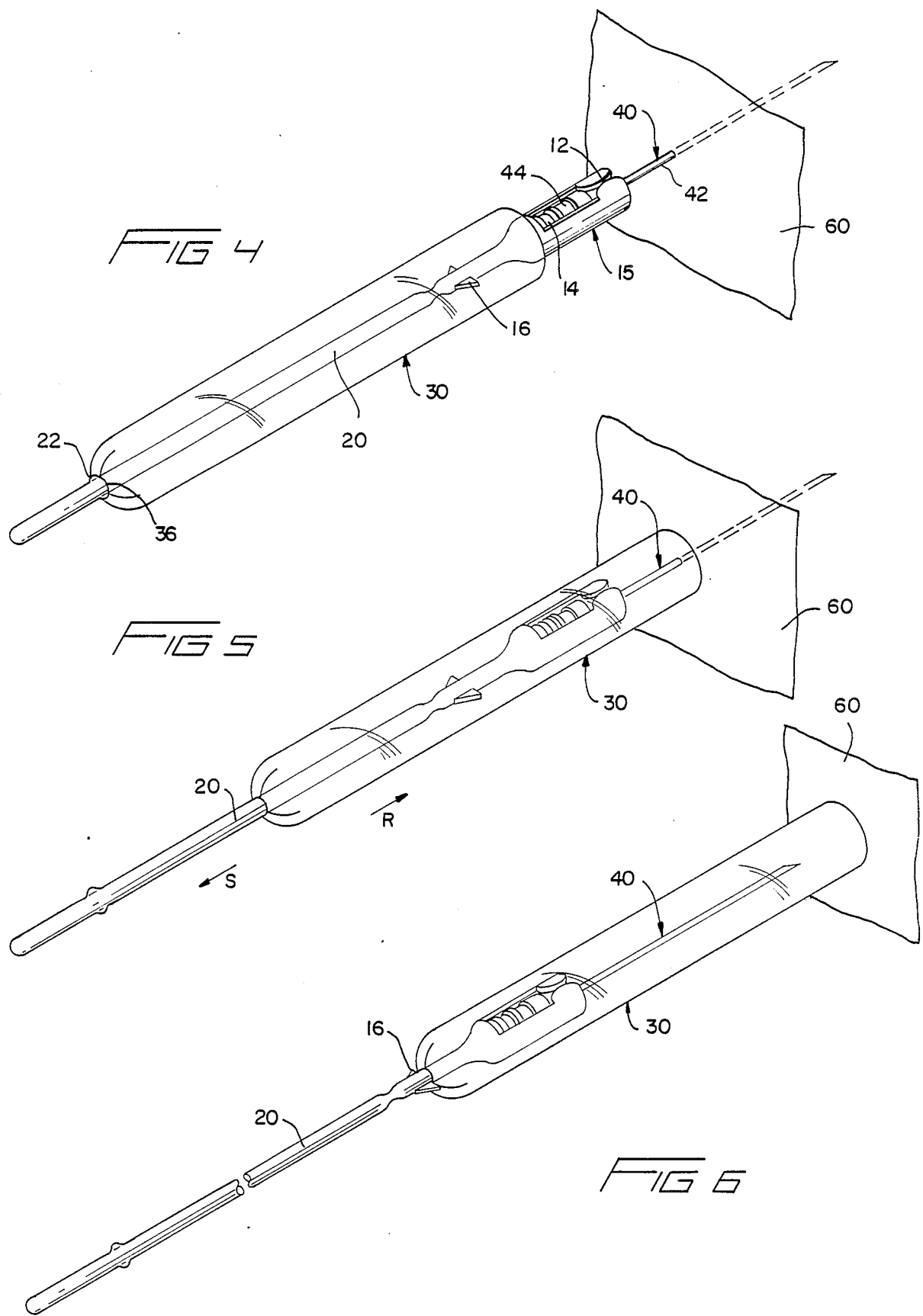

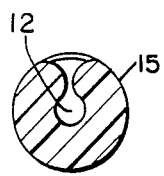 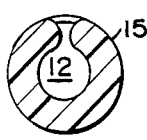 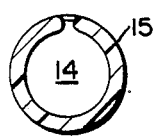 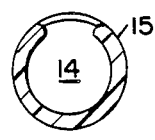
FIG 7
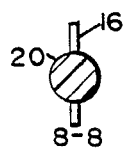
FIG 8
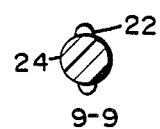
FIG 9
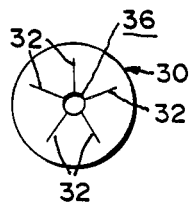
FIG 10

SAFETY DEVICE AND METHOD FOR REMOVAL AND DISPOSAL OF MEDICAL NEEDLES

FIELD OF INVENTION

This invention relates to a protective apparatus and method for safely removing a medical needle, in particular a spinal needle or bone marrow biopsy needle, inserted in a patient for withdrawing or injecting fluids, in such a way as to protect medical personnel from being punctured or even pricked by the removed needle. Additionally, the apparatus of the present invention continues to completely sheath the entire length of a removed needle even when the needle is thrown away, thus protecting all persons who could inadvertently be punctured or pricked.

BACKGROUND OF THE INVENTION

Needle infusion and extraction apparatus for administering or draining fluids from medical patients have been known for years. An ever present danger to medical personnel using needles which have been inserted in patients is the possibility that after a needle has been contaminated by contact with a patient's tissue and fluids, the needle will inject harmful material into another person as a result of an inadvertent breaking of that second person's skin by the contaminated point of the needle. The spreading of fatal hepatitis to medical personnel by inadvertent pricking of their skin with contaminated needles is a well known hazard. Another fatal disease which can be spread by pricking with contaminated needles is Acquired Immune Deficiency Syndrome (AIDS).

The present invention avoids the spreading of diseases through inadvertent skin pricking with contaminated needles by providing a means and method for withdrawing a needle into a convenient sheath, in the form of an external housing, which covers the entire length of the needle. The contaminated needle can then be safely handled and disposed.

SUMMARY OF THE INVENTION

The type of needle apparatus of interest here are spinal needles which have been previously inserted into the spinal canal and are to be withdrawn. Spinal needles are long and somewhat unwieldy because they must penetrate several layers of tissue in order to reach the spinal canal. Spinal needles typically embody an inner needle within an outer needle, the second, internal needle referred to as a stylet. Such needles are employed, for example, in procedures to extract spinal fluid specimens or to inject fluids into the spinal canal for diagnostic or therapeutic purposes.

Procedures employing spinal needles are quite delicate. In order to reach the spinal canal, the needle must puncture and penetrate the skin layers, the subcutaneous fat layer, supraspinous ligaments, interspinal ligaments, ligamentum flavum, epidural space, dura mater, arachnoid and enter the subarachnoid space. In order to penetrate all of these tissues, the needle must be inserted in the space between vertebrae. Because of the delicacy of the insertion of such needles, the procedure is conducted by hand and the needle is typically not connected to any other apparatus, unlike a hypodermic needle which typically must only penetrate skin and soft tissues.

When the spinal needle is to be removed, because of the delicacy of the procedure, the needle is typically not connected to other medical apparatus. Once the needle tip has been withdrawn from the spinal canal, the needle must still be withdrawn through the various tissues it has penetrated in the space between vertebrae. As described below, the present invention provides a needle holder and puller for withdrawing a needle from a patient and a housing which supports the puller and encloses the needle as it is withdrawn.

The invention involves two separate pieces which are assembled to comprise the device. The first piece is a needle pulling assembly comprising a combined needle cradle and pulling rod. The second piece is an external housing designed to fit over the needle cradle and pulling rod structure. The application of this device is as follows. First, the needle is disengaged from any attached structure or specimen collection tube. The stylet is then replaced within the outer needle. Next, the spinal needle is partially withdrawn, so as to remove the sharp, beveled tip from the spinal canal. Then, the needle is engaged at its receptacle end or hub to the needle cradle portion of the two-piece assembly of the instant invention. The external housing portion of the two-piece assembly is moved along the pulling rod portion of the assembly so as to form a sleeve over the needle cradle and exposed length of the needle until the housing rests against the patient's skin. The needle is then extracted by pulling on the pulling rod, while the external housing is held against the patient's skin. When fully withdrawn, the spinal needle is covered over its entire length in sleeve-like fashion by the external housing.

The external housing can be fabricated from a single piece of injection molded plastic. Similarly, the needle cradle with attached pulling rod can be fabricated from a single piece of breakage resistant, but frangible, plastic, preferably rigid or semi-rigid. As fabricated, the external housing and needle cradle of the present invention are relatively low cost parts which, along with the encased contaminated needle, can be safely put in trash collectors for disposal.

In a preferred embodiment, the needle cradle is essentially cylindrical in shape with a cavity provided which will accommodate the receptacle end or hub of the spinal needle. A groove essentially coaxial with the longitudinal center line of the cradle is provided from the cavity to the end of the cradle to accommodate a portion of the shaft of the needle. At the end of the needle cradle opposite to the end with the groove is provided a long pulling rod. The pulling rod has as integral features a detent structure and a lock structure along its length. The lock structure, located closer to the needle cradle, is intended to hold the external housing in place fully enclosing the needle cradle and any engaged needle. The detent structure, located farther from the needle cradle, is intended to hold the external housing in its fully open position so as to accommodate the engagement of a needle to be removed from a patient. The pulling rod also has a waist provided at a position between the detent and lock structures, but located closer to the lock structure, which is intended to be a breaking point for removing the stem of the pulling rod once a needle cradle and needle are fully retracted into the external housing.

In a preferred embodiment, the external housing is essentially test tube-shaped with a first open end which has an interior diameter essentially the same as the remainder of the interior of the external housing and a second open end which is smaller than the diameter of the tube. Radiating from this second opening are a number of slits which are formed or cut into the external housing wall. In actual use, the external housing size would be chosen to be longer than the spinal needle to be removed and enclosed. The interior diameter of the external housing is slightly larger than the exterior diameter of the needle cradle, thereby permitting the external housing to fit in slidable contact with the needle cradle.

The two pieces are assembled by inserting the pulling rod into the first open end of the external housing and then through the smaller second open end at the other end of the housing. The housing is then moved slidably along the pulling rod to a point at which the detent structure is engaged. As thus configured, the assembly is ready to accept a needle to be withdrawn.

The assembly is not associated with a needle until a needle is to be removed from a patient. When a needle is to be removed, the needle is pulled partially out of the patient's body, thereby removing it from the spinal canal. Next, the receptacle end or hub of the needle is engaged by fitting it into the needle cradle cavity, with the needle shaft fitting into the groove extending from the cradle cavity to the end of the cradle. The external housing is then moved slidably along the length of the pulling rod, until the rim of the housing slides past the needle cradle (entrapping the needle hub within the cradle) and contacts the patient's skin. The housing is held pressed against the patient's skin while the pulling rod is pulled in a direction away from the patient. The pulling rod is pulled until the needle cradle reaches the second open end of the external housing and the lock structure is engaged. The spinal needle is thus fully covered along its length by the external housing. The pulling rod can then be broken off at the waist and the entire assembly safely disposed. A plug can be fitted securely into the first open end of the external housing to completely enclose the needle. Alternatively, a cap can be fitted securely over the first open end of the external housing to achieve the same result.

While spinal needles are the focus of the description of this invention, the use of this invention is not limited to spinal needles. It is contemplated that the invention can be used with other needle types such as bone marrow biopsy needles which can be held by the invention at the handle or hub end. In such an application, the needle cradle of the needle pulling assembly would be configured to hold the handle of a bone marrow biopsy needle. The external housing would be enlarged to permit passage of both the handle and needle into the housing. Otherwise, the invention would operate identically as that described for spinal needles.

BRIEF DESCRIPTION OF THE DRAWINGS

The novel features of the invention will be more readily associated with the following description when read in conjunction with the appended drawings, in which corresponding components are designated by the same reference numerals throughout the various figures.

FIG. 1 is a perspective drawing of the assembled device according to the present invention;

FIG. 2 is a perspective drawing of the needle cradle and pulling rod structure;

FIG. 3 is a perspective view of the external housing;

FIG. 4 is a perspective view of the assembly configured with a spinal needle engaged prior to the commencement of withdrawal of the needle using the assembly;

FIG. 5 is a perspective view of the assembly configured with a spinal needle engaged and with withdrawal of the needle commenced;

FIG. 6 is a perspective view of the assembly configured with a spinal needle engaged and fully withdrawn;

FIG. 7 is a sectional view of the cross sections at several axial locations along the needle cradle;

FIG. 8 is a sectional view of the pulling rod taken along line 8—8 and an end view of the lock structure for engaging the assembly in the fully retracted position;

FIG. 9 is a sectional view of the stem taken along line 9—9 and an end view o the detent structure for engaging the assembly in the fully open position;

FIG. 10 is an end view of the external housing structure.

DETAILED DESCRIPTION OF THE INVENTION

An assembled protective device according to a preferred embodiment of the invention is shown in FIG. 1 where it is generally designated by reference numeral 5. The assembled protective device is comprised of two component pieces, a needle pulling assembly 10 (as shown in FIG. 2) and an external housing 30 (as shown in FIG. 3). The protective device is assembled by inserting the pulling rod 20 of the needle pulling assembly 10 into the external housing 30 first open end 34 and then through external housing second open end 36. The external housing 30 is then moved slidably along the pulling rod 20.

The needle pulling assembly 10 has two primary features, a needle cradle 15 and a pulling rod 20. The needle cradle 15 has a cavity 14 and a longitudinal groove 12 extending from the cavity 14 to the end of the needle cradle 15. The cavity 14 and the longitudinal groove 12 are designed to accommodate the receptacle end or hub of a spinal needle and a portion of the needle shaft. The needle pulling assembly 10 also has a detent structure 22 and a lock structure 16. A waist 18 is provided on the pulling rod 20 for breaking off a stem portion 24 once the pulling rod 20 has been fully withdrawn and locked into place in the external housing 30.

The external housing 30 is a hollow, essentially test tube-shaped structure with a first open end 34. At the other end of the external housing 30, is a second open end 36, from which radiate one or more slits 32 in the housing 30.

In a preferred embodiment, the interior diameter of external housing 30 is so dimensioned with respect to the exterior diameter of needle cradle 15, to allow the needle cradle 15 to move in slidable contact with external housing 30.

FIG. 4 illustrates the initial stage of operation of the invention. A needle 40 has already been partially removed from a patient by withdrawing it from the spinal canal. The needle 40 with its shaft 42 and hub 44 is then engaged with the needle pulling assembly 10 by fitting the hub 44 into the cavity 14 and the shaft 42 into the groove 12 of the needle cradle 15. The external housing 30 at the second open end 36 is held in place along the pulling rod 20 by detent structure 22.

FIG. 5 illustrates the withdrawal of the needle 40 using the protective device 5. The external housing 30 is moved in a sliding fashion along the pulling rod 20 toward the patient, shown by arrow R, until it contacts the patient's skin 60. The external housing 30 is held against the patient's skin 60 while the pulling rod 20 is pulled in a direction away from the patient's skin 60, shown by arrow S. The direction of motion of the external housing 30 with respect to the pulling rod 20 is essentially coaxial with the longitudinal axis of the external housing 30 defined by the alignment of the first open end 34 in the external housing 30 and the second open end 36 in the external housing 30.

FIG. 6 illustrates the protective device 5 with a needle 40 fully withdrawn into the external housing 30. The pulling rod 20 is shown locked into place by lock structure 16. The needle 40 is covered its entire length by the external housing 30.

Both the needle pulling assembly 10 and the external housing 30 can be made of a variety of rigid or semi-rigid materials. In a preferred embodiment each would be made of breakage resistant plastic. Such breakage resistant plastic would be, however, frangible at points such as the waist 18.

Referring again to FIG. 2, the needle pulling assembly 10 features are described in more detail. The needle cradle 15 is shown to have a longitudinal groove 12 extending into the cavity 14 from the end opposite the pulling rod 20. The cavity 14 is designed to accommodate the receptacle end or hub of a spinal needle. The longitudinal groove 12 is designed to accommodate a portion of the shaft 42 of the needle 40. The cavity 14 is essentially cylindrical in shape, conforming to the general outside contours of the needle cradle 15. The cavity 14 has a side port or aperture through which the hub 44 of the needle 40 is inserted. Similarly, the groove 12 is open at one side, in order to accommodate a portion of the shaft 42 of the needle 40. At the base of the cradle 15, the cross-sectional diameter of the groove 12 is narrowed to permit only the shaft 42 of the needle 40 to exit the cradle 15. The hub 44 of the needle 40 is thus restrained from passing through the base of the cradle 15.

FIG. 7 shows four cross-sectional views of the needle cradle 15 at Sections A—A, B—B, C—C, and D—D of FIG. 2. These sectional views further illustrate the spaces into which the hub 44 and shaft 42 of the needle 40 are accommodated.

FIG. 8 shows a cross-section of the pulling rod 20 taken along line 8—8 of FIG. 2 and an end view of the lock structure 16 which is used to lock the needle pulling assembly 10 into place once the needle 40 has been fully withdrawn.

FIG. 9 shows a cross-section of the stem 24 taken along line 9—9 of FIG. 2 and an end view of the detent structure 22 which is used to hold the needle pulling assembly 10 in place in order for a needle 40 to be engaged prior to pulling.

FIG. 10 shows an end view of the external housing 30, with the second open end 36 and slits 32 radiating from the second open end 36. This second open end 36 is intended to accommodate the pulling rod 20 so that the needle pulling assembly 10 can be drawn back and forth through the external housing 30. The slits 32 radiating from the open end 36 are intended to allow the external housing 30 to be deformed so as to permit passage of the lock structure 16 and detent structure 22 through the hole 36.

An external housing 30 could be fabricated so as to have a wider exterior diameter at the first open end 34 which is held against the patient than the exterior diameter for the remainder of the external housing 30. Such a wider diameter would serve to form a more stable base to rest against the patient.

An end plug (not shown) could be frictionally fitted securely within the first open end 34 of the external housing 30. Alternatively, an end cap, of such dimensions to fit securely over the first open end 34 of the external housing 30 could also be provided.

It is envisioned that arrangements other than cradle 15 for holding the needle may be employed. An example, not shown, would be to grasp the hub 44 of the needle 40 with a plurality of prongs spatially arranged at the end of the pulling rod 20. The needle cradle 15 can also be enlarged to hold the barrel and plunger of a syringe (not shown), as well as the needle hub 44 itself.

Likewise, non-cylindrical external housing 30 structures can be envisioned which would still accommodate a needle pulling assembly 10 with an engaged needle 40 and also act as a support while the needle 40 is being withdrawn.

The above discussion has centered on spinal needles. Other needles, such as those used for insertion into bones and other body parts can be accommodated by this invention. For example, in such applications, the needle cradle cavity would be shaped to hold the handle of a bone marrow biopsy needle. The external housing would be sized to permit the passage of the bone marrow biopsy handle and needle into the housing.

The above discussion and related illustrations of the present invention are directed primarily to preferred embodiments and practices of the invention. However, it is believed that numerous changes and modifications in the actual implementation of the concepts described herein will be apparent to those skilled in the art, and it is contemplated that such changes and modifications may be made without departing from the scope of the invention as defined by the following claims.

What is claimed is:

1. An apparatus separate from a spinal or bone marrow biopsy needle for protection from such a needle upon withdrawal from a patient comprising:
    a housing component and
    a needle pulling component comprising cradle means for engaging the receptacle end of a spinal or bone marrow biopsy needle to be withdrawn from a patient and pulling rod means attached to said cradle means
    said housing component having an open distal end defining a passage for said cradle and a proximal end defining a passage for said pulling rod
    said housing means being dimensional to slidably engage said cradle and to enclose said needle upon withdrawal from a patient.

2. An apparatus as defined by claim 1 wherein said pulling rod comprises at least one lock structure to secure said needle pulling component in a predetermined position within said housing component.

3. An apparatus as defined by claim 2 wherein said pulling rod is provided with a lock structure to secure said cradle in a position appropriate for engagement of the receptacle end of a needle inserted into a patient.

4. An apparatus as defined by claim 2 wherein said pulling rod is provided with a lock structure to secure said needle and cradle within said housing after withdrawal of said needle from a patient.

5. A apparatus as defined by claim 1 or 2 wherein said pulling rod comprises a predetermined break point.

6. A apparatus as defined by claim 5 wherein said break point is provided by a stem and waist structure.

7. An apparatus as defined in claim 1 wherein said cradle means comprises a hollow enclosure to receive the receptacle end of a needle.

8. An apparatus as defined by claim 7 wherein said cradle is provided with access means for the receptacle end of a needle, said access means comprising an opening into said enclosure and an associated longitudinal groove defining a passage for a needle shaft, said groove extending from said enclosure to the distal end of said cradle.

9. A method for removing a medical needle, having a hub end, from a patient to avoid needle pricks and support said needle being removed, comprising the steps of:
 (a) fitting said hub end to a needle cradle attached to a pulling rod;
 (b) sliding an external housing along said pulling rod until said external housing is pressed against said patient; and
 (c) pulling said pulling rod in a direction away from said patient until said medical needle is withdrawn from said patient into said external housing.

* * * * *